United States Patent
Hegedus

(10) Patent No.: US 7,976,308 B2
(45) Date of Patent: Jul. 12, 2011

(54) DENTAL WEDGES AND METHODS

(76) Inventor: Gyula Julius Hegedus, Langley (CA)

( * ) Notice: Subject to any disclaimer, the term of this patent is extended or adjusted under 35 U.S.C. 154(b) by 2 days.

(21) Appl. No.: 11/691,499

(22) Filed: Mar. 27, 2007

(65) Prior Publication Data

US 2008/0241787 A1   Oct. 2, 2008

(51) Int. Cl.
*A61C 7/00* (2006.01)

(52) U.S. Cl. .......................................... 433/149

(58) Field of Classification Search ............... 433/39, 433/148, 149; 132/321, 329
See application file for complete search history.

(56) References Cited

U.S. PATENT DOCUMENTS

| | | | | |
|---|---|---|---|---|
| 2,867,905 A | * | 1/1959 | Meacham | 433/149 |
| 2,891,313 A | * | 6/1959 | Crowley | 433/149 |
| 3,563,253 A | * | 2/1971 | Barman | 132/329 |
| 3,590,814 A | * | 7/1971 | Bennett et al. | 601/139 |
| 3,660,902 A | * | 5/1972 | Axelsson | 433/142 |
| 4,271,854 A | * | 6/1981 | Bengtsson | 132/329 |
| 4,337,041 A | * | 6/1982 | Harsany | 433/149 |
| 4,577,649 A | * | 3/1986 | Shimenkov | 132/329 |
| 6,402,514 B1 | * | 6/2002 | Fischer et al. | 433/149 |
| 2004/0014006 A1 | * | 1/2004 | Garrison et al. | 433/149 |
| 2005/0272005 A1 | * | 12/2005 | Schaffner et al. | 433/149 |

* cited by examiner

*Primary Examiner* — Cris L. Rodriguez
*Assistant Examiner* — Michael R Ballinger

(57) ABSTRACT

Improved dental wedge having curved elongate body approximating the anatomical curvature of a tooth undergoing repair to hold the matrix in conformity with the anatomical curvature of said tooth. The wedges comprising a curved elongate body having proximal and distal ends and tapering from the proximal end to the distal end, the elongate body further having a bottom surface, an inside surface and an outside surface opposite the inside surface, the curvature of the elongate body being towards the inside surface, and the bottom surface adjacent the insertion portion being curved upwards relative to the remainder of the bottom surface. The elongate body may be generally triangular in cross-section, and the inside surface is concave and the outside surface is convex transversely to the elongate body.

14 Claims, 3 Drawing Sheets

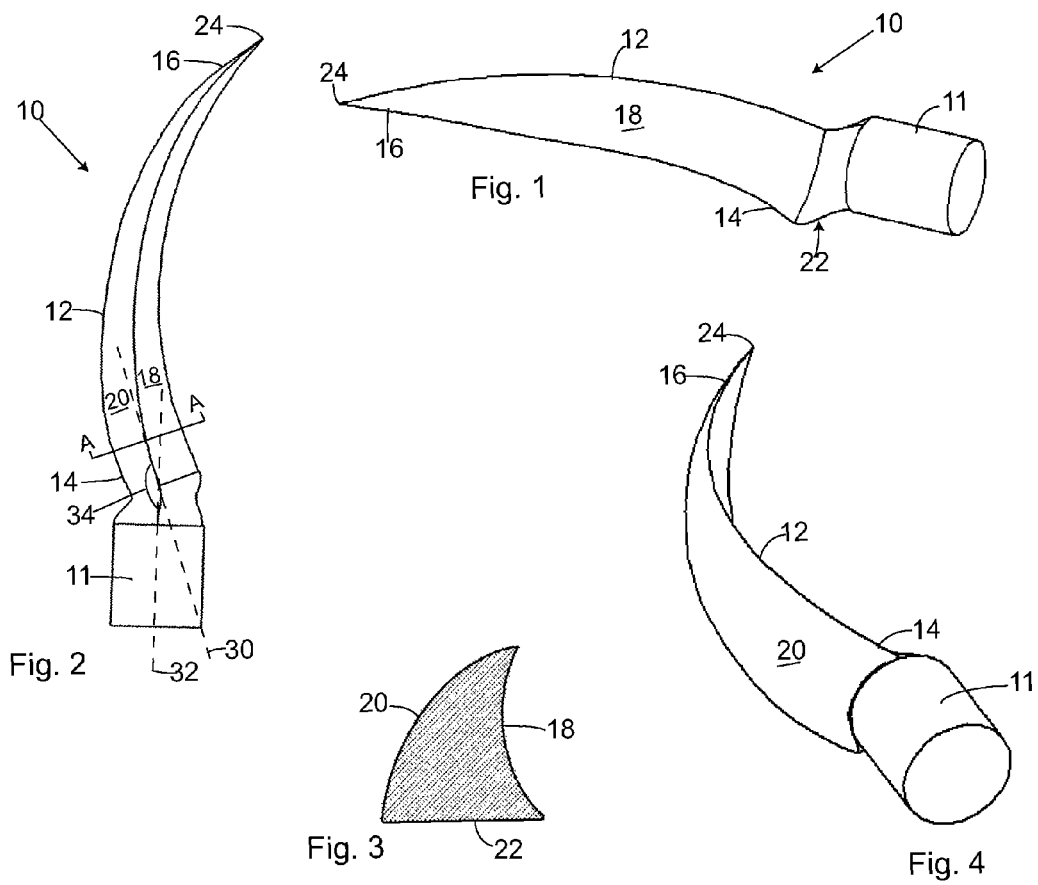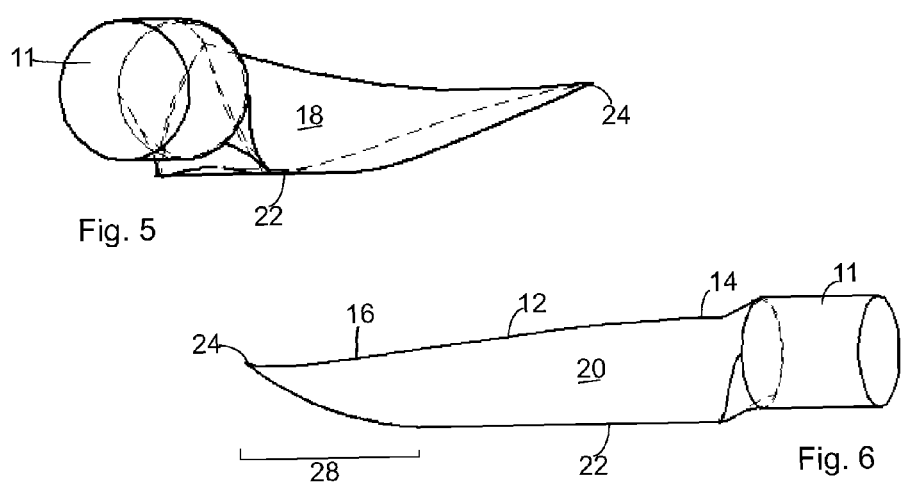

DENTAL WEDGES AND METHODS

REFERENCE TO DISCLOSURE DOCUMENT

Reference is made herein to Disclosure Document No. 597338, titled Dental Wedge System with Clockwise and Counter Clockwise Curvatures, received in the United States Patent and Trademarks Office on Mar. 22, 2006.

THE FIELD OF THE INVENTION

The present invention is in the field of dental retention devices. In particular, the present invention relates to dental wedges that are used for separating teeth and for holding matrix bands against teeth during dental procedures.

BACKGROUND OF THE INVENTION

Dental wedges are often used during many restorative dental procedures. When decay is located between two teeth, tooth material is removed between the two teeth in preparation for restoration. A matrix band, which typically comprises a thin metallic or plastic strip that is flexible and can be bent around the tooth being restored, is then placed between the two teeth to form a wall to contain the restorative dental material. However, many matrix bands are not adapted well to the bottom or gingival portions of the tooth being restored. In order to obtain a good fit with the tooth and adaptation of the matrix band to the gingival portion, a wedge is often forced into the area between the matrix band and an adjacent tooth. The purpose of the wedge is to press the gingival portion of the matrix band against the tooth, preventing the restorative material from being forced beyond the cavity preparation, which could produce a permanent irritation and possible periodontal abscess. The wedge may also be used to help force the teeth apart, allowing for the thickness of the matrix band. After placement of the restorative material, the matrix band and wedge are removed allowing the slight separation of the teeth to come together. Typically, wedges are relatively small pieces of material made of wood or plastic and are usually picked up with forceps or other small tweezer-like appliance and forced between an adjacent tooth and the matrix band. The dental wedges of the prior art comprise a straight elongate body, which may or may not have an upward curvature (i.e. in the vertical plane) to minimize the damage to the gum tissue when the wedge is inserted into the interproximal area between the teeth. An inherent problem with dental wedges of the prior art is that they fail to keep the matrix band in proper placement during the filling procedure since the wedges of the prior art to not conform well to the anatomical surface curvature of the teeth. Accordingly, there is a need in the art for an improved dental wedge for holding the matrix band in proper placement in a manner that conforms the matrix band to the external anatomical curvature of the tooth undergoing repair.

SUMMARY OF THE INVENTION

The present invention is directed to improved dental wedges for use in dental procedures. In particular, dental wedges of the invention have a curved elongate body in the horizontal plane wherein the curvature approximates the anatomical curvature of the tooth undergoing repair, which enables the dental wedges of the present invention to hold the matrix band in proper placement in a manner that conforms the matrix band to the anatomical curvature of the tooth.

In one aspect, the present invention provides a dental wedge comprising a curved elongate body having a proximal end and a distal end, the elongate body tapering from the proximal end to the distal end and the distal end defining an insertion portion, the elongate body further having a bottom surface, an inside surface and an outside surface opposite the inside surface, the curvature of the elongate body being towards the inside surface, and the bottom surface adjacent the insertion portion being curved upwards relative to the remainder of the bottom surface. Preferably, the elongate body is generally triangular in cross-section and the bottom surface, the outside surface and the inside surface converge towards the insertion portion to an apex. Preferably, inside surface is concave transversely to the elongate body and the outside surface is convex transversely to the elongate body. In some embodiments, particularly when the dental wedges are to be used in association with human teeth, the elongate body is in the range of 10 mm. to 15 mm. in length and the curvature of the elongate body defines an arc having a radius in the range of 10 mm. to 15 mm. Preferably, there is included a head portion, which may be cylindrical, attached to the proximal end of the elongate body and adapted to being grasped by a suitable tool or implement to facilitate placement and removal of the dental wedge.

It will become apparent that the curved dental wedges of the present invention can have either a clockwise or counter clockwise curvature, and each particular curvature can be used against one tooth face (mesial or distal) when inserted from one direction (buccal or lingual), and the other tooth face when inserted from the other direction. Therefore, to simplify the selection of which curvature of dental wedge to use against a particular tooth face when the wedge is to be inserted from a particular side for the dental practitioner, the present invention also provides dental wedge dispensing devices and selection methods. Accordingly, the present invention also provides a dental wedge dispensing device comprising a central planar member having a peripheral edge, a plurality of dental wedges, each dental wedge having a head portion attached to a curved elongate body portion, a plurality of breakable connector portions, each connector portion connecting the head portion of a dental wedge to the peripheral edge of the central planar member, and a protective member connected to the central planar member and coplanar therewith, the protective member surrounding the plurality of dental wedges to protect the wedges from accidental dislodgment from the central planar member. In some embodiments, the central planar member is divided into four visual quadrants such that each visual quadrant corresponds to a dental quadrant in a mammalian mouth and all of the elongate bodies of the dental wedges associated with any one of said four visual quadrants are curved in the same direction. There may be included a first indicator marking in each quadrant corresponding to either a mesial or distal anatomical tooth surface, a second indicator marking in each quadrant corresponding to either a buccal or lingual anatomical side of a tooth such that the first indicator marking and the second indicator marking within any one of the visual quadrants together indicate the anatomical tooth surface against which a dental wedge associated with said visual quadrant can be applied when said dental wedge is inserted from a particular side of said anatomical sides of the tooth that is located within the corresponding dental quadrant to said visual quadrant. In some embodiments, the central planar member is a disk and the protective member is a ring that encircles the plurality of dental wedges. Preferably, the device is a unitary body made from injection molded thermoplastic material.

In another aspect, the present invention provides methods of indicating to a dental practitioner the anatomical tooth surface against which a curved dental wedge can be applied comprising providing a member that is divided into four portions wherein each portion corresponds to a dental quadrant in a mammalian mouth, providing a plurality of curved dental wedges removably associated with each potion wherein all of the dental wedges associated with any one portion are curved in the same direction, providing a first indicator marking on each portion corresponding to either a mesial or distal anatomical tooth surface, and providing a second indicator marking on each portion corresponding to either a buccal or lingual anatomical side of a tooth, wherein the first indicator marking and the second indicator marking on any one portion together indicate the anatomical tooth surface against which a dental wedge associated with said portion can be applied when said dental wedge is inserted from a particular side of said anatomical sides of the tooth located within the corresponding dental quadrant to said portion.

BRIEF DESCRIPTION OF THE DRAWINGS

For a better understanding of the present invention and to show more clearly how it may be carried into effect, reference will now be made by way of example to the accompanying drawings in which:

FIG. 1 is an upper right perspective view of an embodiment of a dental wedge of the present invention having a counterclockwise orientation;

FIG. 2 is top plan view of an embodiment of a dental wedge of the present invention having a clockwise orientation;

FIG. 3 is a cross-section of the dental wedge in FIG. 2 taken along line A-A;

FIG. 4 is an upper left perspective view of the dental wedge in FIG. 2;

FIG. 5 is a lower right perspective view of the dental wedge in FIG. 2;

FIG. 6 is a right side elevational view of the dental wedge in FIG. 2;

DETAILED DESCRIPTION OF THE PREFERRED EMBODIMENTS

Figure 7:
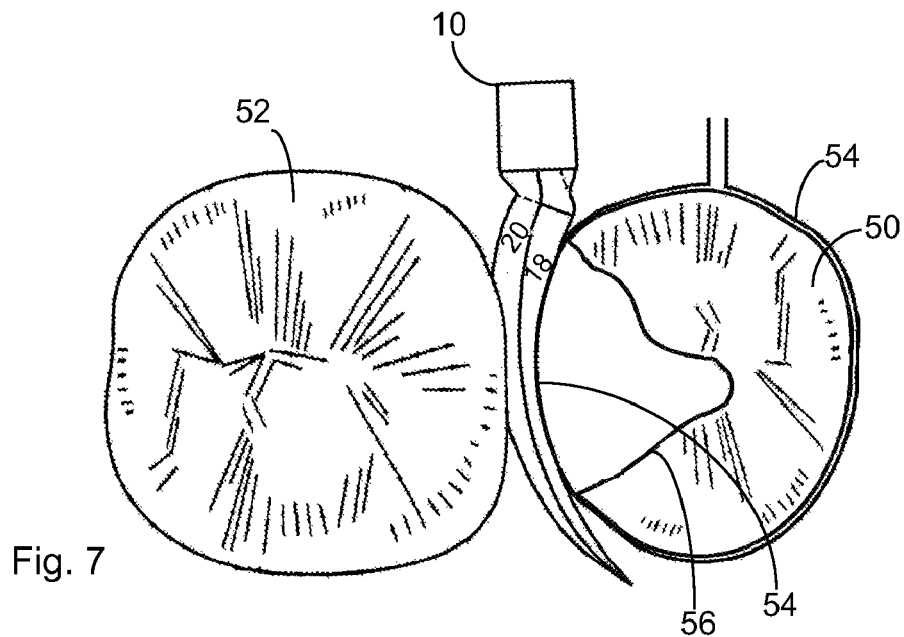
FIG. 7 is a top plan view of the dental wedge in FIG. 1 having been inserted into the interproximal space between two teeth.

For the purposes of promoting an understanding of the principles of the invention, reference will now be made to the exemplary embodiments illustrated in the drawings, and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would occur to one skilled in the relevant art and having possession of this disclosure, are to be considered within the scope of the invention. Therefore, specific details disclosed herein are not to be interpreted as limiting, but rather as a basis for the claims and as a representative basis for teaching one skilled in the art to employ the present invention.

FIGS. 1-6 illustrate a presently preferred embodiment of a dental wedge of the invention for insertion into the interproximal space between adjacent teeth during restorative dental work. As shown, dental wedge 10 comprises a head portion 11 coupled to a curved elongate body 12 that extends from a proximal end 14 to a distal insertion end 16 and is curved along a horizontal plane. The elongate body 12 defines an inside surface 18 on the inside of the curvature of the elongate body 12, an outside surface 20 on the outside of the curvature, and a bottom surface 22 that is adjacent the inside surface 18 and the outside surface 20.

In the depicted embodiment and as shown in FIG. 3, the elongate body 12 has a generally triangular cross-sectional shape and gradually tapers from the larger proximal end 14 to the smaller distal end 16, converging to an apex or tip 24. Hence the inside surface 18, the outside surface 20 and the bottom surface 22 converge to the tip 24. The distal end 16 of elongate body 12 further defines a leading insertion portion 28 that spans from the tip 24 to approximately one-third the length of the elongate body 12 towards the proximal end 14. The bottom surface 22 located within the insertion portion 28 curves upward, relative to the remainder of the bottom surface, towards the tip 24 (as best illustrated in FIG. 6) to minimize the damage to the gum tissue as the wedge is inserted into the interproximal area between the teeth. Alternatively, the upward curving of bottom surface 22 within the insertion portion 28 may also be achieved by providing an upward curvature (i.e. in the vertical plane) of the whole of the insertion portion 28.

As depicted, head 11 is cylindrical in shape and is generally coplanar (FIG. 6) with the curved elongate body 12 in a horizontal plane. Head 11 is also substantially longitudinally aligned with a longitudinal axis 30 of the proximal end 14 such that the angle 34 defined by the longitudinal axis 32 of the head 11 and longitudinal axis 30 is preferably in the range of 15° and 25°. The head 11 facilitates gripping of the dental wedge 10, using fingers, forceps, pliers or other appropriate tool or instruments, which enables dental practitioners to insert the dental wedge 10 into the interproximal space between adjacent teeth and to subsequently remove the dental wedge 10 therefrom once the restorative procedure is complete. It should be appreciated that the shape of head 11 can vary in size and shape and is not limited to the cylindrical shape shown in the figures. It is also contemplated that in some embodiments, head 11 might be omitted altogether, in which case the gripping of the dental wedge could be accomplished by grasping proximal end 14 of the elongate body, or by other means.

In preferred embodiments, the length of the elongate body 12 is in the range of 10 mm. to 15 mm. and the curvature of the elongate body 12 approximately defines an arc having a radius in the range of 10 mm. to 15 mm., thereby approximating the varying sizes and anatomical curvatures encountered in most human teeth. However, it is contemplated that embodiments of the present invention may vary in size and in the curvature of the elongate member 12 depending on the size of the teeth in conjunction with which those embodiments are to be used, such as for example, in dental repair performed on other mammals.

As best depicted in FIG. 3, the inside surface 18 is concave transversely to the elongate body and the outside surface 20 is convex transversely to the elongate body. In one aspect, the concave inside surface 18 and the convex outside surface 20, together with the tapering of the elongate body 12 towards the distal end facilitate some flexibility of the elongate body 12 towards the direction of the curvature so as to allow the elongate body 12 to flex inward. In another aspect, the concave and convex surfaces enable two dental wedges to fit together, the convex surface of one wedge abutting the concave surface of the other wedge, such as when two wedges are required to effectively conform the matrix to the outline of the damaged tooth, as illustrated in FIG. 8, such as when the interproximal space is too wide for one wedge alone.

FIG. 7 illustrates the presently preferred embodiment of a dental wedge in use during restorative work. A tooth 50 undergoing repair has been prepared and a matrix band 54 has been placed around the tooth 50 to span the opening to cavity 56 for retaining the filling material within the cavity. Dental wedge 10 is inserted into the interproximal space between a tooth 50 and an adjacent healthy tooth 52 such that the inside surface 18 abuts the matrix band 54 and holds it against the cavity opening. The curvature of the elongate member 12 conforms the matrix band to the outer anatomical shape of the tooth. The bottom surface 22 rests on the gums in the interproximal space and the outside surface 20 abuts the surface of the adjacent tooth 52 to push the inside surface 18 against the matrix band 54.

Figure 8:
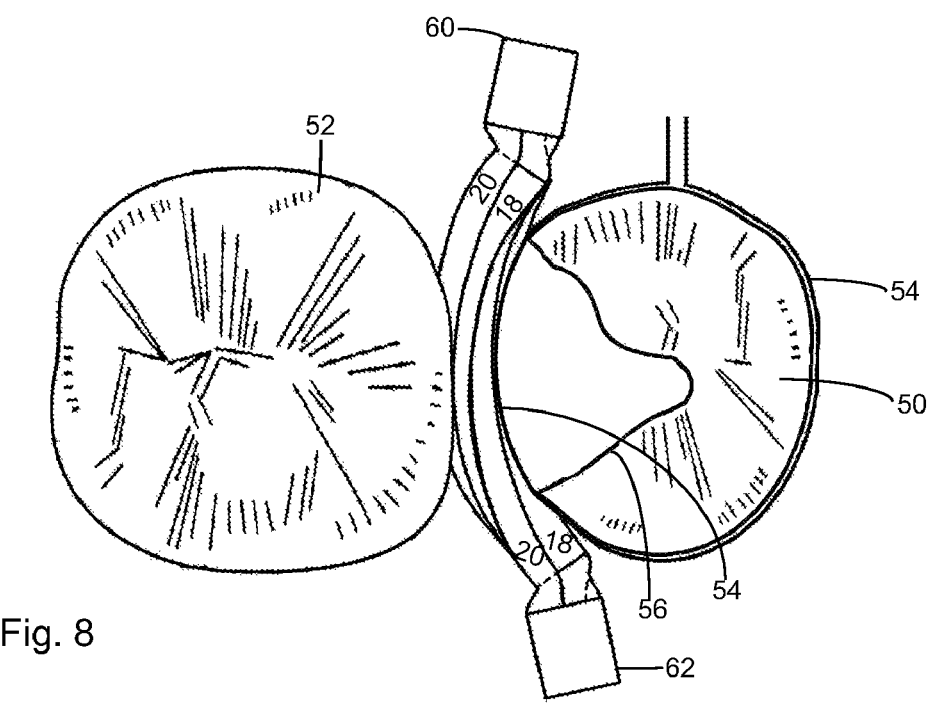
FIG. 8 is a top plan view of the dental wedge in FIG. 1 and the dental wedge of FIG. 2 after both have been inserted into the interproximal space between two teeth.

FIG. 8 illustrates two dental wedges 60 and 62 in accordance with the presently preferred embodiment used together to hold matrix band 54 against the opening of cavity 56 of the tooth 50 undergoing repair. Two dental wedges may be used together, for example, when the interproximal space between teeth 50 and 52 is too wide to enable one dental wedge alone to perform the function of holding the matrix band in place. The concave surfaces 18 and convex surfaces 20 enable the two dental wedges to fit together in close conformity, the convex surface of one wedge resting within the concave surface of the other wedge, such that the two wedges resist being separated due to the lateral compression forces applied to them.

According to a preferred embodiment, dental wedge 10 is composed of a thermoplastic material that is preferably formed by injection molding as an efficient and relatively inexpensive way to produce dental wedges in large quantities. Preferably, the thermoplastic material is a medical grade polypropylene; however, it is contemplated that other suitable material and modes of manufacture may also be used. Preferably, the material used in the manufacture of the dental wedges would enable some lateral flexing of the elongate body 12 and some upward flexing of the insertion portion 28 to allow conformity with anatomical structures encountered during insertion of the dental wedge, but would provide rigidity at the proximal end 14 and in the head 11.

The curvature of the elongate body 12 may be either clockwise (as in FIG. 2) or counterclockwise (as in FIG. 1). Hence, a dental wedge having a clockwise curvature can be used to repair one half of the tooth surfaces within a patient's mouth, and a dental wedge with counter-clockwise curvature can be used to repair the other half of the tooth surfaces. In order to provide a quick and convenient reference as to which tooth surfaces a dental wedge having a particular curvature can be used in conjunction with, the present invention further provides dental wedge display and dispensing systems and dental wedge kits.

Figure 9:
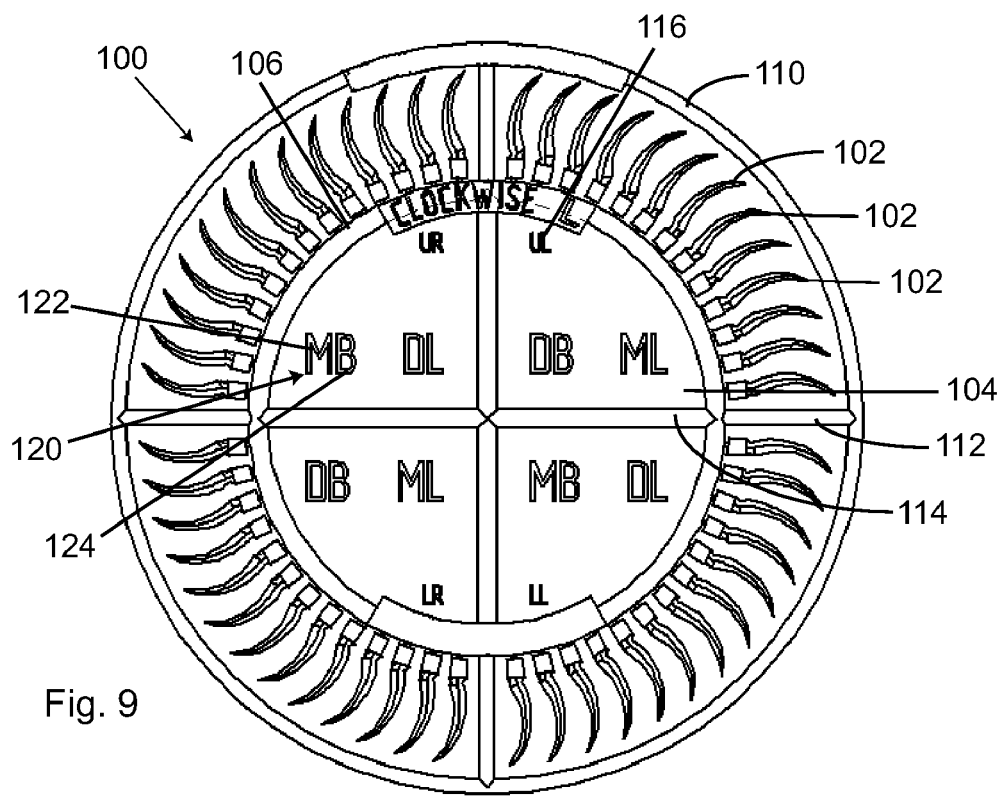
FIG. 9 is a top plan view of an embodiment of a dental wedge dispensing and display system in accordance with the present invention in which the dental wedges are in a clockwise orientation.
Figure 10:
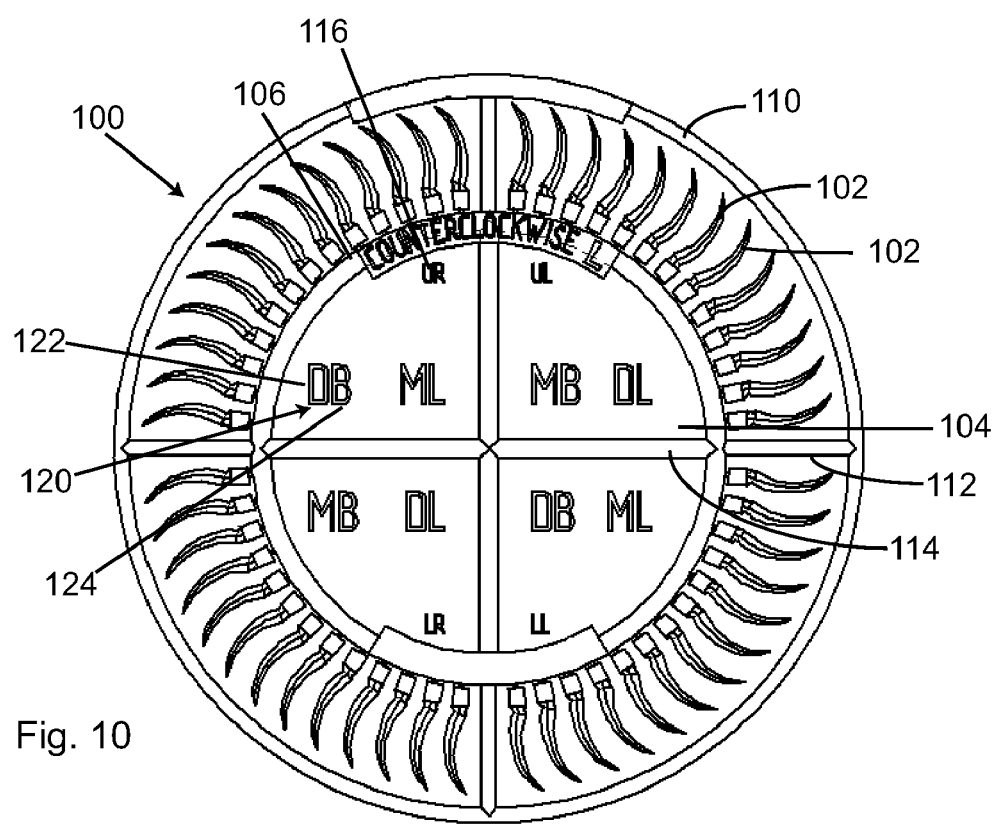
FIG. 10 is a top plan view of an embodiment of a dental wedge dispensing and display system in accordance with the present invention in which the dental wedges are in a counterclockwise orientation.

Referring to FIGS. 9 & 10, there is illustrated a presently preferred embodiment of a dental wedge selection and dispensing device 100 in accordance with the present invention. Dental wedge selection and dispensing device 100 comprises a planar member or central disk 104 having a peripheral edge 106 on which are attached a plurality of dental wedges 102 in a manner such that the longitudinal axis of each dental wedge is in the same plane as the central disk 104. FIG. 9 depicts a selection and dispensing device 100 having dental wedges with elongate bodies curved in a clockwise direction, and FIG. 10 depicts a selection and dispensing device 100 having dental wedges with elongate bodies curved in a counter-clockwise direction. As depicted, the head 11 of each dental wedge is connected to the peripheral edge 106 by a thin strip of material which is breakable so that each dental wedge 102 can be removed from the central disk 104 by bending or twisting the whole dental wedge in relation to a central disk. A protective member or ring 110 that is coplanar with the central disk 104 is provided attached to the peripheral edge 106 by supports 112. The protective ring 110 surrounds or encircles the plurality of dental wedges 102 to protect said wedges from being accidental dislodged from the central disk, such as by dropping of the unit. In a preferred embodiment, the entire selection and dispensing device 100, together with the dental wedges 102 thereon, is made as a unit by injection molding of a thermoplastic material, such as a medical grade polypropylene.

The central planar member or disk 104 is divided into four portions or visual quadrants by divider ridges 114 whereby each quadrant on the central disk corresponds to one of the four anatomical or dental quadrants in a mammalian mouth: right maxillary or upper right quadrant (UR); left maxillary or upper left quadrant (UL); right mandibular or lower right quadrant (LR); and left mandibular or lower left quadrant (LL). A quadrant marker 116 in each visual quadrant identifies its corresponding anatomical quadrant. Each quadrant further includes orientation indicators 120 which comprise two components: a first indicator or tooth face identifying component 122, and a second indicator or directional component 124. The tooth face identifying component 122 corresponds to the mesial (M) or distal (D) anatomical side surfaces of a tooth. The directional component 124 corresponds to the direction from which the dental wedge is to be inserted (i.e. the direction in which the head 11 faces): buccal (B) or lingual (L). Therefore, the quadrant markers 116 in conjunction with the orientation indicators 120 quickly and efficiently inform the dental practitioner as to which tooth surfaces the dental wedges having a particular curvature may be used against to hold a matrix band in place. For example, referring to the clockwise oriented dental wedges of FIG. 9, if a dental practitioner seeks to repair a tooth located in the right maxillary or upper right quadrant of a patient's mouth, he or she would refer to the visual quadrant on the central disk having quadrant indicator 116 of "UR", which corresponds to this anatomical quadrant. Then, the practitioner would refer to the orientation indicators 120 within that quadrant, which in the "UR" quadrant are "MB" and "DL". The "MB" orientation indicator 120 informs the practitioner that the clockwise curved dental wedges associated with this visual quadrant may be used against a matrix band on the mesial surface of the tooth if the wedge is inserted from the buccal side of the tooth. The "DL" orientation indicator 120 informs the practitioner that the clockwise curved dental wedge may be used against a matrix band on the distal surface of the tooth if the wedge is inserted from the lingual side of the tooth. If, in fact, the dental practitioner wants to hold a matrix band in place on the distal tooth surface and to insert the wedge from the buccal side of the tooth, then he or she must use a counter-clockwise wedge since, as shown in FIG. 10, the orientation indicator 120 having the desired tooth face identifying component 122 of "D" for distal and directional component 124 of "B" for buccal appears in the "UR" quadrant of the counterclockwise wedges.

The orientation indicators 120 in conjunction with the division of the central disk 104 into quadrants that corresponds to the anatomical or dental quadrants of a mouth provide a quick reference to assist the dental practitioner in selecting the appropriate wedge—either clockwise or counterclockwise—depending on the quadrant of the mouth the damage tooth is located, the particular tooth surface that is being restored, and the direction from which the dental wedge is to be inserted.

While some preferred forms of the invention have been described by way of example, it should be appreciated that modifications and improvements can occur without departing from the scope of the appended claims.

I claim:

1. A dental wedge for tight placement into the interproximal space between adjacent teeth during dental reconstruction to hold a matrix band so that it conforms to an anatomical tooth surface of one of said teeth as a result of the device being wedged against the other of said teeth, the dental wedge having an elongate body with a proximal end and a distal end, the elongate body being generally triangular in cross-section and tapering from the proximal end to the distal end, the distal end defining an insertion portion, the elongate body further having a bottom surface, an inside surface and an outside surface opposite the inside surface, wherein the bottom surface and the inside surface define a first edge where they meet, the outside surface and the inside surface define a second edge where they meet, and the outside surface and the bottom surface define a third edge where they meet, the elongate body being curved in a horizontal plane along its entire length towards the inside surface such that the inside surface is adapted to hold the matrix band in conformance to the anatomical tooth surface, and the proximal end defining a terminal head portion adapted to being grasped by a suitable tool or implement to facilitate placement and removal of the dental wedge between said teeth, and wherein the inside surface is concave transversely to the elongate body entirely from the first edge to the second edge, and the outside surface is convex transversely to the elongated body entirely from the second edge to the third edge.

2. The device of claim 1 wherein the bottom surface adjacent the insertion portion is curved upwards relative to the remainder of the bottom surface.

3. The device of claim 2 wherein the bottom surface, the outside surface and the inside surface converge towards the insertion portion to an apex.

4. The device of claim 3 wherein the elongate body is in the range of 10 mm. to 15 mm. in length.

5. The device of claim 4 wherein the horizontal curvature of the elongate body defines an arc having a radius in the range of 10 mm. to 15 mm.

6. The device of claim 5 wherein the head portion is cylindrical.

7. The device of claim 6 wherein a longitudinal axis of the head portion is substantially longitudinally aligned with a longitudinal axis of the elongate body at the proximal end such that the angle defined by said axes is in the range of 15° and 25°.

8. A dental wedge system having first and second dental wedges for being used for tight placement into the interproximal space between adjacent teeth during dental reconstruction to hold a matrix band so that it conforms to an anatomical tooth surface of one of said teeth as a result of the devices being wedged against the other of said teeth, the first dental wedge having a first elongate body and the second dental wedge having a second elongate body, each elongate body having a proximal end and a distal end, each elongated body being generally triangular in cross-section and tapering from the proximal end to the distal end and the distal end defining an insertion portion, each elongate body further having a bottom surface, an inside surface and an outside surface opposite the inside surface, wherein the bottom surface and the inside surface define a first edge where they meet, the outside surface and the inside surface define a second edge where they meet, and the outside surface and the bottom surface define a third edge where they meet each elongate body being curved in a horizontal plane along its entire length towards the inside surface such that the inside surface is adapted to hold the matrix band in conformance to the anatomical tooth surface, and each proximal end defining a terminal head portion adapted to being grasped by a suitable tool or implement to facilitate placement and removal of each dental wedge between said teeth, wherein the inside surface is concave transversely to the elongated body entirely from the first edge to the second edge, and the outside surface is convex transversely to the elongated body entirely from the second edge to the third edge, and wherein the horizontal curvature of the first elongate body is in a clockwise direction to enable the clockwise dental wedge when inserted from a buccal side to be used to hold the matrix band in conformance to a mesial anatomical tooth surface in an upper right or a lower left mouth quadrant, or in conformance to a distal anatomical tooth surface in a lower right or an upper left mouth quadrant, and the horizontal curvature of the second elongate body is in a counterclockwise direction to enable the counterclockwise dental wedge when inserted from a buccal side to be used to hold the matrix band in conformance to a mesial anatomical tooth surface in the upper left or the lower right mouth quadrant, or in conformance to a distal anatomical tooth surface in the upper right or the lower left mouth quadrant.

9. The system of claim 8 wherein the bottom surface of each elongate body adjacent the insertion portion is curved upwards relative to the remainder of the bottom surface.

10. The system of claim 9 wherein on each elongate body the bottom surface, the outside surface and the inside surface converge towards the insertion portion to an apex.

11. The system of claim 10 wherein each elongate body is in the range of 10 mm. to 15 mm. in length.

12. The system of claim 11 wherein the horizontal curvature of the elongate body defines an arc having a radius in the range of 10 mm. to 15 mm.

13. The device of claim 12 wherein the head portion is cylindrical.

14. The system of claim 13 wherein a longitudinal axis of the head portion is substantially longitudinally aligned with a longitudinal axis of the elongate body at the proximal end such that the angle defined by said axes is in the range of 15° and 25°.

* * * * *